United States Patent [19]

Stern

[11] 4,380,543
[45] Apr. 19, 1983

[54] ANTIMICROBIAL 8-CYANO-6,7-DIHYDRO-5-METHYL-1-OXO-1H,5H-BENZO[ij]QUINOLIZINE-2-CARBOXYLIC ACIDS

[75] Inventor: Richard M. Stern, Cottage Grove, Minn.

[73] Assignee: Riker Laboratories, Inc., St. Paul, Minn.

[21] Appl. No.: 318,928

[22] Filed: Nov. 6, 1981

[51] Int. Cl.$^3$ ............... A61K 31/47; C07D 455/04
[52] U.S. Cl. ................................. 424/258; 546/94; 546/165; 546/166
[58] Field of Search ..................... 546/94; 424/258

[56] References Cited

U.S. PATENT DOCUMENTS 3,896,131   7/1975   Gerster ................. 546/94

FOREIGN PATENT DOCUMENTS 55-27204    9/1980   Japan ..................... 546/94
55-131632   9/1980   Japan ..................... 546/94
55-59121   11/1980   Japan ..................... 546/94
55-61776   11/1980   Japan ..................... 546/94
55-106776  12/1980   Japan ..................... 546/94
56-131630   2/1981   Japan ..................... 546/94
56-131629   5/1981   Japan ..................... 546/94
56-131631   5/1981   Japan ..................... 546/94
56-135807   5/1981   Japan ..................... 546/94

OTHER PUBLICATIONS

March, J., *Advanced Organic Chemistry*, McGraw Hill, New York, 1968, p. 313.
Fieser, L. et al., *Reagents for Organic Synthesis*, John Wiley, New York, 1967, pp. 394–395.

*Primary Examiner*—Richard A. Schwartz
*Attorney, Agent, or Firm*—Cruzan Alexander; Donald M. Sell; Carolyn A. Bates

[57] ABSTRACT

The compounds 8-cyano-6,7-dihydro-5-methyl-1-oxo-1H,5H-benzo[ij]quinolizine-2-carboxylic acid and 8-cyano-6,7-dihydro-9-fluoro-5-methyl-1-oxo-1H,5H-benzo[ij]quinolizine-2-carboxylic acid are disclosed as potent antimicrobial agents. Pharmaceutically-acceptable carboxylate salts, esters, acyl chlorides, amides and alkylaminoalkyl ester salts of the acids are also disclosed.

5 Claims, No Drawings

ANTIMICROBIAL 8-CYANO-6,7-DIHYDRO-5-METHYL-1-OXO-1H,5H-BENZO[ij]QUINOLIZINE-2-CARBOXYLIC ACIDS

TECHNICAL FIELD

This invention relates to antimicrobial compounds which are 6,7-dihydro-5-methyl-1-oxo-1H,5H-benzo[ij]quinolizine-2-carboxylic acids and salts, esters and amides thereof. A process and intermediates for preparing the compounds are also included within the scope of the invention. Further aspects of the invention relates to the use of the compounds as antimicrobial agents and pharmaceutical formulations containing the compounds.

BACKGROUND ART

U.S. Pat. No. 3,896,131 broadly describes 6,7-dihydro-5-methyl-1-oxo-1H,5H-benzo[ij]quinolizine-2-carboxylic acids as active antimicrobial agents. The compound 10-cyano-6,7-dihydro-5-methyl-1-oxo-1H,5H-benzo[ij]quinolizine-2-carboxylic acid is specifically disclosed in the aforementioned patent (Example 71). It has now been found that the corresponding novel 8-cyano compound is much more potent and has a broader spectrum of antimicrobial activity than the 10-cyano compound. Accordingly, the 8-cyano compounds of the present invention are much safer and more economical to use than the 10-cyano compound of the prior art.

DESCRIPTION OF THE INVENTION

This invention relates to novel 8-cyano-6,7-dihydro-5-methyl-1-oxo-1H,5H-benzo[ij]quinolizine-2-carboxylic acids of the formula

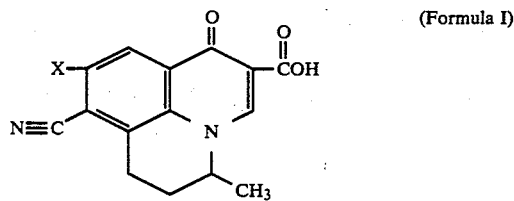

(Formula I)

wherein X is fluoro or hydrogen; and pharmaceutically acceptable carboxylate salts, amides, esters, acyl chlorides and alkylaminoalkyl ester salts thereof. These compounds are useful as antimicrobial agents.

It is well known in the art that pharmaceutically acceptable salts such as alkali metal, alkaline earth, aluminum, iron and other metal and amine salts of pharmaceutically active acids are generally equivalent to the acids in terms of activity, and in some cases may even offer advantages in absorption, formulation and the like. Carboxylate salts of the free acid compounds of the invention are readily prepared by reacting the acid with a base and evaporating to dryness. The base may be organic, e.g., sodium methoxide or an amine, or inorganic, e.g., sodium hydroxide. Alternatively, the cation of a carboxylate salt, e.g., sodium, may be displaced by a second cation such as calcium or magnesium when the salt of the second cation is more insoluble in the selected solvent.

The esters and amides of the acid compounds of the invention are useful for modifying the solubility and persistence properties of the acids, and also for the synthetic preparation of the acids. The preferred esters are alkyl esters and alkylaminoalkyl esters where the alkyl group contain 1 to 4 carbon atoms. Especially preferred are alkylaminoalkyl esters which will form salts, e.g., hydrochlorides, such as dimethylaminoethyl esters. The preferred amides are those wherein the —OH group of the acids is replaced by —NR$_1$R$_2$ where R$_1$ and R$_2$ are independently hydrogen or an alkyl group having 1 to 4 carbon atoms.

The free acid compounds of the invention are presently preferred due to their higher levels of antimicrobial activity.

The antimicrobial activity of the compounds of the invention can be demonstrated by the known, standard plate dilution method for bacterial susceptibility to antibiotics. The culture medium employed permits susceptibility testing of fastidious microorganisms towards antibiotics, sulfonamides and other chemotheraeutic agents. Tryptone soy agar (oxoid) of the following composition is the culture medium.

| Oxoid tryptone | 15 g. |
|---|---|
| Oxoid soy peptone | 5 g. |
| Sodium chloride | 5 g. |
| Oxoid agar-agar No. 3 | 15 g. |
| Water | 1 liter |

Using this test, the compounds of the invention have been found to have a broad spectrum of activity against gram-positive and gram-negative microorganisms.

The compounds of the invention are active against microorganisms either in the absence or presence of 10 percent horse serum.

The test procedure used to determine activity as employed in connection with the present invention provides information on the amount of a compound required to give complete inhibition, partial inhibition or no inhibition of microbial growth on the agar plates. In the tests, the test compound is added to the agar medium to give concentrations of zero, one, ten and one hundred milligrams per liter. A series of plates with these concentrations is prepared. Ten percent horse serum is added to one series of such plates. Aliquots of broth culture of any of twelve species of microorganisms are inoculated onto the agar plates containing the various compound concentrations. The plates are incubated at 37° C. in a 10 percent carbon dioxide atmosphere for 18 to 24 hours. The microbial growth on each plate is read visually, and minimal inhibitory concentrations are recorded. Some of the microorganisms which are used in this test are:

1. *Staphylococcus aureus*
2. *Bacillus subtilis*
3. *Escherichia coli*
4. *Pseudomonas aeruginosa*
5. *Streptococcus sp.* *
6. *Asperigillus niger*
7. *Candida albicans*
8. *Acinetobacter lwoffi*
9. *Acinetobacter anitratum*
10. *Klebsiella pneumoniae*
11. *Streptococcus fecaelis*
12. *Serratia marcescens*

*Strains isolated from dental caries in rats or hamsters at the National Institute of Dental Health and grown in PFY or APT agar.

All of the compounds of the invention possess antimicrobial activity towards one or more of the above microorganisms.

Compounds of the invention have also shown activity against one or more anaerobic bacteria, for example, Bacteroides sp. and Clostridium sp. The compounds have also shown activity against *Erwinia amylovora*, a gram-negative organism responsible for the plant disease known at fire blight. The compound where X is hydrogen has also shown activity against *Trichophyton rubrum* and *Epid. floccosum*

It will be understood by those skilled in the art that the species used are representative indicator species, as it would be impractical to screen against all microorganisms. It is well known in the art that broad spectrum activity can be predicted on the basis of activity shown against selected representative species of microorganisms.

The compounds of the invention are active when administered orally to animals. They are excreted in the urine, and are effective urinary tract antibacterials in mammals. Oral activity of the compounds of the invention has been demonstrated in vivo in rats. The models used predict activity in pulmonary infections, soft tissue infections, bacteremia and burn wounds.

The compounds of the invention are active against microorganisms in vitro or topically. In vitro activity is useful in itself, since antimicrobial agents may be used for disinfecting and sterilizing, e.g., medical and dental equipment, as components of disinfecting solutions.

The acute oral toxicity of the compounds of the invention generally is low compared with the effective oral dose, and they have excellent therapeutic ratios.

The acidic compounds of the invention and their salts are ordinarily white or yellowish to brown crystalline or amorphous materials when purified. They are substantially insoluble in water, lower alcohols or hydrocarbons and are more soluble in halogenated solvents, N,N-dimethylformamide and the like. The esters and amides are generally somewhat more soluble in organic solvents. The alkali metal salts have appreciable solubility in water and lower alcohols.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing objects to be treated therein, or by local application to an infected area.

The amount of compound to be used to treat, e.g., a microbial urinary infection or other systemic infection by oral treatment will be an effective amount less than a toxic amount. The amount to be administered to control an infection will depend on the species, sex, weight, physical condition and many other factors, but this judgment is well within the skill of the medical art. Usually the amount will be less than 100 mg/kg per dose. Conveniently this is administered in the form of conventional pharmaceutical preparations such as capsules, tablets, emulsions, solutions and the like. Excipients, fillers, coatings, etc., are generally employed with tablets or capsules as is well known in the art.

It is known to the art that antimicrobial agents are used as growth promoters in various animal and bird species. Although not yet verified, it is inferred from their outstanding antimicrobial activity that the compounds of the invention can be used for this purpose also. The compounds of the invention may also be used for the control of microbial (e.g., *Erwinia amylovora*) infections of plants, e.g., by spraying or dusting formulations of these compounds on the affected area.

The carboxylic acid compound of Formula I where X is hydrogen is prepared starting with the known compound 5-acetamidoquinaldine according to the following synthetic sequence.

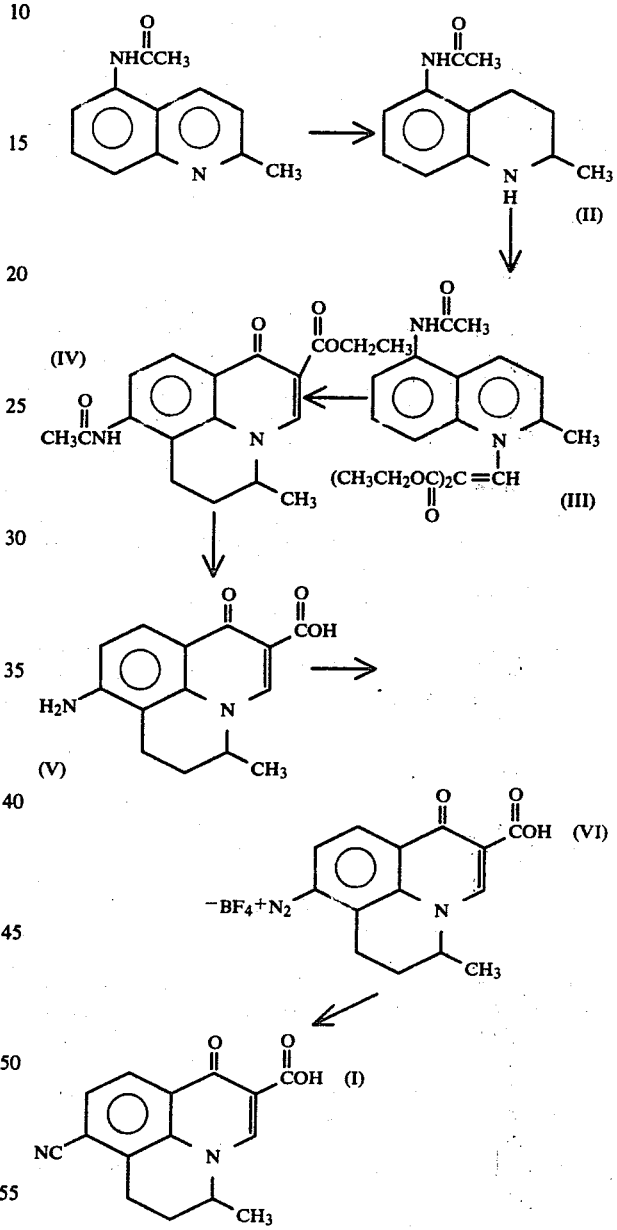

The first step in the reaction sequence is reduction using chemical or catalytic reduction methods to provide the novel compound 5-acetamido-1,2,3,4-tetrahydroquinaldine of Formula II. Catalytic reduction using hydrogen gas and a catalyst such as rhodium on carbon or platinum on charcoal is the presently preferred method. The reduction is carried out using the relatively low pressure of a Parr apparatus. The compound to be reduced is dissolved in a suitable non-reactive solvent such as ethanol or ethyl acetate and acidified with acetic acid.

The second step in the synthetic sequence is the condensation of 5-acetamido-1,2,3,4-tetrahydroquinaldine with a dialkyl alkoxymethylenemalonate such as diethyl ethoxymethylenemalonate by heating the two reactants, without solvent, at 100° to 200° C., and preferably at about 160° C., for one to five hours. The resulting novel intermediate of Formula III generally is not isolated or purified. Instead, polyphosphoric acid is added and the solution is heated at 100° to 140° C. to effect a further condensation to provide the novel ester of Formula IV. The next step involves hydrolysis of the ester group and the acetamido group of the compound of Formula IV to provide the novel compound of Formula V. The primary aromatic amino group of the compound of Formula V is diazotized in the presence of fluoroboric acid, and the novel solid diazonium fluoroborate of Formula VI is isolated. The fluoroborate salt is reacted by heating with a cyanide salt, preferably cuprous cyanide, in a very polar solvent such as dimethyl sulfoxide to provide the final product of Formula I.

In order to prepare the compound 8-cyano-6,7-dihydro-9-fluoro-5-methyl-1-oxo-1H,5H-benzo-[ij]quinolizine-2-carboxylic acid, one starts by nitrating 2-fluorobenzoic acid. Nitration with concentrated nitric and concentrated sulfuric acids at moderate temperatures (15°–25° C.) provides 2-fluoro-5-nitrobenzoic acid. Catalytic reduction, e.g., with palladium on charcoal catalyst, provides 5-amino-2-fluorobenzoic acid. Condensation of this aromatic amine with crotonaldehyde in the presence of ferrous sulfate heptahydrate and sodium m-nitrobenzene-sulfonate provides 5-carboxy-6-fluoroquinaldine. The carboxyl group is reacted with thionyl chloride to provide the carboxyl chloride which is reacted with ammonium hydroxide to provide 5-carboxamido-6-fluoroquinaldine. Dehydration of the carboxamido group in pyridine with trifluoroacetic anhydride in an inert solvent such as dichloromethane provides 5-cyano-6-fluoroquinaldine. This intermediate is reduced catalytically in the presence of platinum on carbon in a mixture of acetic acid and a lower alkanol such as isopropanol. The product is 5-cyano-6-fluorotetrahydroquinaldine. This intermediate condenses with diethyl ethoxymethylenemalonate to yield an intermediate of Formula III where the 5-position is substituted by cyano rather than acetamido and the 6-position is substituted by fluoro rather than hydrogen. Condensation in polyphosphoric acid provides the benzo[ij]quinolizine ring, but the cyano group may be partially hydrolyzed and again require dehydration with pyridine and trifluoroacetic anhydride. Hydrolysis of the carboxylic ester group in the 2 position may also be required to obtain the desired 8-cyano-6,7-dihydro-9-fluoro-5-methyl-1-oxo-1H,5H-benzo[ij]quinolizine-2-carboxylic acid.

The compound wherein X is hydrogen may also be prepared using the latter route starting with the known compound 5-carboxylquinaldine. It has now been found that this is the preferred synthetic route for both of the compounds of the invention.

Esters and amides of the acids of Formula I are readily prepared by converting the acid to the novel acid chloride, e.g., by reaction with thionyl chloride, then reacting with suitable alcohols, amines or ammonia.

The invention is further illustrated by the following non-limiting examples.

EXAMPLE 1

To a solution of 21 g of 5-acetamidoquinaldine in ethanol was added 1 g of 5% platinum on charcoal and 20 ml of acetic acid. The mixture was reacted with hydrogen gas in a Parr apparatus at 25° C. for one day. The mixture was filtered, and the filtrate was concentrated to provide a residue which was partitioned between chloroform and ten percent sodium hydroxide. The organic layer was dried, and evaporated to provide a residue which was crystallized from a mixture of chloroform and heptane. The product was white crystals of the novel compound 5-acetamido-1,2,3,4-tetrahydroquinaldine, m.p. 164°–166° C. The structural assignment was confirmed by infrared spectral analysis. Analysis: Calculated for $C_{12}H_{16}N_2O$: %C, 70.6; %H, 7.9; %N, 13.7; Found: %C, 70.7; %H, 8.1; %N, 13.8.

EXAMPLE 2

A mixture of 19 g of 5-acetamido-1,2,3,4-tetrahydroquinaldine and 24.0 g of diethyl ethoxymethylenemalonate was heated at 160° C. for 2 hours. The product obtained was not purified. To the mixture was added 60 g of polyphosphoric acid, and the mixture was heated at 100° C. for one hour. To the mixture was added 400 ml of warm water. The mixture was basified and cooled. The solid residue was separated by decantation to provide ethyl 8-acetamido-6,7-dihydro-5-methyl-1-oxo-1H,5H-benzo[ij]quinolizine-2-carboxylate. Next the solid was dissolved in 20 ml of methanol, and to this solution was added 80 ml of ten percent sodium hydroxide solution. The solution was heated on a steam bath for one hour, followed by the addition of 20 ml of concentrated ammonium hydroxide. The solution was acidified to pH 6 with acetic acid. A solid precipitate formed which was separated by filtration and recrystallized from aqueous N,N-dimethylformamide to provide brown crystals of 8-amino-6,7-dihydro-5-methyl-1-oxo-1H,5H-benzo[ij]quinolizine-2-carboxylic acid. The structure was confirmed by infrared and nuclear magnetic resonance spectral analysis.

EXAMPLE 3

Step A

To 250 ml of a hot 48% aqueous solution of fluoroboric acid was added 50 g of 8-amino-6,7-dihydro-5-methyl-1-oxo-1H,5H-benzo[ij]quinolizine-2-carboxylic acid. The solution was gradually cooled to 0° C., and 16.8 g of sodium nitrite in 50 ml of water was added slowly with vigorous stirring. After stirring about 30 minutes at 0° C., 250 ml of ice water was added. Stirring was continued for about thirty minutes. The solid was separated by filtration and washed sequentially with an isopropanol-fluoroboric acid mixture, isopropanol, an isopropanol-diethyl ether mixture, and diethyl ether. The product, 8-diazonium-6,7-dihydro-5-methyl-1-oxo-1H,5H-benzo[ij]quinolizine-2-carboxylic acid fluororborate, was a gold solid.

Step B

A mixture of 81 g of cuprous cyanide and 57 g of sodium cyanide in 550 ml of dimethyl sulfoxide was heated on a steam bath until the solids were dissolved. After cooling to 25° C., 55 g of 8-diazonium-6,7-dihydro-5-methyl-1-oxo-1H,5H-benzo-[ij]quinolizine-2-carboxylic acid fluoroborate in 275 ml of dimethyl sulfoxide was added slowly with rapid stirring. The temperature was maintained below 30° C. for one hour after the completion of the addition. The mixture was then poured into 5 liters of water. The tan solid was separated by filtration and recrystallized from N,N-dimethylformamide to provide 8-cyano-6,7-dihydro-5-methyl-1-oxo-1H,5H-benzo[ij]-quinolizine-2-carboxylic acid, m.p. 300° C. Analysis: Calculated for $C_{15}H_{12}N_2O_3$: %C 67.2; %H, 4.5; %N, 10.4; Found: %C, 67.1; %H, 4.8; %N, 10.1.

EXAMPLE 5

A mixture of 0.0037 mole (1.0 g) of 8-cyano-6,7-dihydro-5-methyl-1-oxo-1H,5H-benzo[ij]quinolizine-2-carboxylic acid, 10 ml of thionyl chloride and 1 drop N,N-dimethylformamide was heated at its reflux temperature for 15 minutes, then evaporated to dryness. The product was 8-cyano-6,7-dihydro-5-methyl-1-oxo-1H,5H-benzo-[ij]quinolizine-2-carboxyl chloride, a gray solid.

EXAMPLE 6

To the product of Example 5 was added 25 ml of ethanol, and the mixture was heated on a steam bath for about one hour. The solvent was evaporated to provide a residue which was recrystallized from ethanol to produce ethyl 8-cyano-6,7-dihydro-5-methyl-1-oxo-1H,5H-benzo[ij]quinolizine-2-carboxylate, m.p. 249°-51° C. Analysis: Calculated for $C_{17}H_{16}N_2O_3$. %C, 68.9; %H, 5.4; %N, 9.4; Found: %C, 69.0; %H, 5.4; %N, 9.2.

EXAMPLE 7

Sodium ethoxide was prepared by reacting 0.0038 mole (0.09 g) of sodium metal and 50 ml of ethanol by stirring at 25° C. for 1.5 hours. This sodium ethoxide was reacted with 0.0037 mole (1.0 g) of 8-cyano-6,7-dihydro-5-methyl-1-oxo-1H,5H-benzo[ij]quinolizine-2-carboxylic acid by heating at reflux for 10 minutes. The mixture was evaporated to provide a residue which was recrystallized from aqueous isopropanol. The product was sodium 8-cyano-6,7-dihydro-5-methyl-1-oxo-1H,5H-benzo[ij]-quinolizine-2-carboxylate, m.p. >300° C. Analysis: Calculated for $C_{15}H_{11}N_2NaO_3 \cdot \frac{1}{4}H_2O \cdot \frac{1}{8}C_3H_8O$: %C, 61.0; %H, 4.5; %N, 8.9; Found: %C, 61.0; %H, 4.8; %N, 9.3.

EXAMPLE 8

Sodium ethoxide was prepared by reacting 0.0038 mole (0.09 g) of metallic sodium was 50 ml of ethanol. This solution was added to a stirred suspension of 0.0037 mole (1 g) of 8-cyano-6,7-dihydro-5-methyl-1-oxo-1H,5H-benzo[ij]quinolizine-2-carboxylic acid in 25 ml of ethanol. After stirring 15 minutes, 25 ml of water was added and the mixture was filtered. To the filtrate was added 0.4 g of calcium chloride dissolved in 5 ml of water. The solution was partially evaporated to provide 10 ml of a mixture which was filtered to separate the solid. The solid was dried under vacuum to provide calcium 8-cyano-6,7-dihydro-5-methyl-1-oxo-1H,5H-benzo[ij]quinolizine-2-carboxylate, m.p. >300° C. Analysis: Calculated for $(C_{15}H_{11}N_2O_3)_2Ca \cdot \frac{1}{2}H_2O$: %C, 61.7; %H, 4.0; %N, 9.6; Found: %C, 61.7; %H, 3.8; %N, 9.4.

EXAMPLE 9

Part A

To a mixture of 225 ml (3.75 mole) of concentrated sulfuric acid and 225 ml (3.3 mole) of concentrated nitric acid was added 100 g (0.713 mole) of 2-fluorobenzoic acid. The temperature was maintained between 15° and 25° C. The mixture was stirred for an hour after completion of the addition. The temperature rose to about 30° C. The solution was decanted into 4 liters of ice water to provide 111.1 g of white crystals of 2-fluoro-5-nitrobenzoic acid. The structural assignment was confirmed by infrared and nuclear magnetic resonance spectral analyses.

Part B

One hundred eleven g of 2-fluoro-5-nitrobenzoic acid was dissloved in 1 liter of ethyl acetate. To this solution was added 5 g of 5 percent palladium on charcoal. The mixture was hydrogenated on a Parr apparatus for 24 hours at 20° C. at 50 psi of hydrogen. The theoretical amount of hydrogen was absorbed. The solution was filtered, then evaporated to dryness to provide a tan residue of 95.2 g of 5-amino-2-fluorobenzoic acid.

Part C

A mixture of 95.2 g of 5-amino-2-fluorobenzoic acid, 74.3 g (0.33 mole) of sodium meta-nitrobenzenesulfonic acid, 46.2 g of ferrous sulfate heptahydrate and 660 ml of 9 N hydrochloric acid was heated to 90°-95° C. Crotonaldehyde (96%) 77 g, (1.0 mole) was added dropwise over 2.5 hours with vigorous stirring and maintenance of temperature just below reflux. After stirring an additional half hour the solution was filtered hot through a glass wool plug. The filtrate was cooled to 30° C. and treated with decolorizing charcoal and filtered. The clear filtrate was cooled in ice with stirring to provide a light yellow solid. The solid was separated by filtration, washed with acetone and dried. The solid was dissolved in 400 ml of hot water, and a solution of 50 g of sodium acetate in 100 ml of water was added. The product was 58.2 g of cream crystals of 5-carboxyl-6-fluoroquinaldine. The structural assignment was confirmed by infrared and nuclear magnetic resonance spectral analyses.

Part D

A mixture of 58.2 g of 5-carboxyl-6-fluoroquinaldine and 200 ml of thionyl chloride with 2.5 ml of N,N-dimethylformamide was heated on a steam bath for 10 minutes. The mixture was allowed to sit at 20° C. for 0.5 hour, followed by the addition of 400 ml of diethyl ether. The white solid precipitate was separated by filtration, washed with diethyl ether and dried. This product was the acyl chloride derivative. It was added in small portions to 200 ml of cold concentrated ammonium hydroxide with rapid stirring. The mixture was stirred for 20 minutes at 20° C. The product was separated by filtration, washed with water and dried to provide 49 g of 5-carboxamido-6-fluoroquinaldine. The structural assignment was confirmed by infrared and nuclear magnetic resonance spectral analyses.

Part E

To a mixture of 49 g of 5-carboxamido-6-fluoroquinaldine, 44.5 ml of pyridine and 250 ml of dichloromethane were added 37 ml of trifluoroacetic anhydride while maintaining the temperature between 24° and 27° C. The addition required about 6 hours. The solution was stirred at 20° C. for 16 hours, and 100 ml of cold 1 N sodium hydroxide solution was added. The layers were separated and the organic layer was washed with water and dried over magnesium sulfate. The organic solution was evaporated and the residue was triturated with water to provide a tan solid. The solid was separated by filtration and washed with water to provide 42.2 g of 5-cyano-6-fluoroquinaldine. The structural assignment was confirmed by infrared spectral analysis.

Part F

A solution of 42.2 g of 5-cyano-6-fluoroquinaldine and 150 ml of glacial acetic acid and 150 ml of isopropyl alcohol was formed by heating. The mixture was cooled to about 35° C. and 7.5 g of sodium acetate and 3 g of 5% platinum on carbon were added. The mixture was hydrogenated on a Parr apparatus for 72 hours at 30 psi. The theoretical amount of hydrogen was 41 psi. The actual hydrogen absorbed was 43 psi. The catalyst was separated by filtration, and the filtrate was evaporated to provide an oil. Ice water was added. The pH of the mixture was adjusted to 8 with sodium hydroxide and sodium bicarbonate. The solid product was separated by filtration, washed with water and dried. The product was 5-cyano-6-fluorotetrahydroquinaldine (40.2 g of cream crystals). The structural assignment was confirmed by infrared spectral analysis.

Part G

A mixture of 40.2 g of 5-cyano-6-fluorotetrahydroquinaldine and 69 g of diethyl ethoxymethylenemalonate in 300 ml of xylene was heated at its reflux temperature for 28 hours using a Dean Stark trap to remove xylene. The xylene removed was replaced with equal volumes of fresh xylene. After this reaction period, the reaction mixture was evaporated to 250 ml volume. Five hundred ml of heptane were added. The solution was filtered, and the filtrate was treated with 350 ml of hexane. On cooling and stirring, cream crystals of the desired condensation product were obtained. The product was washed with a xylene-hexane (1:4) mixture and then with hexane to provide 58.3 g of diethyl 2-[N-(5-cyano-6-fluorotetrahydroquinaldinyl]-methylenemalonate. The structural assignment was confirmed by infrared and nuclear magnetic resonance spectral analyses.

Part H

A portion of the product from Part G (5.0 g) was combined with 15 g of polyphosphoric acid, and the mixture was heated at 140° C. for 45 minutes with stirring. The mixture was cooled, and 75 ml of water was added. The mixture was stirred for 30 minutes, and the white solid product 8-cyano-6,7-dihydro-9-fluoro-5-methyl-1-oxo-1H,5H-benzo[ij]quinolizine-2-carboxylic acid as the ethyl ester was obtained. Infrared and nuclear magnetic spectral analyses of this product indicated that the cyano group in the 8 position had been partially hydrolyzed back to the carboxamido group, i.e., the product obtained is a mixture of ethyl 8-cyano-6,7-dihydro-9-fluoro-5-methyl-1-oxo-1H,5H-benzo[ij]-quinolizine-2-carboxylate and ethyl 8-carboxamido-6,7-dihydro-9-fluoro-5-methyl-1-oxo-1H,5H-benzo[ij]-quinolizine-2-carboxylate.

Part I

The product mixture from part H, 4.2 g was suspended in 250 ml of dichloromethane and 4.8 ml of pyridine. To the stirred mixture was added 4 ml of trifluoroacetic anhydride over a period of 10 minutes. The solution was stirred for three hours, and washed with cold 3% sodium hydroxide solution. The solution was dried over magnesium sulfate, treated with decolorizing charcoal and evaporated. The white residue was recrystallized from aqueous N,N-dimethylformamide to provide 2.4 g of white needles of ethyl 8-cyano-6,7-dihydro-9-fluoro-5-methyl-1-oxo-1H,5H-benzo[ij]-quinolizine-2-carboxylate, m.p. 260°–263° C. Analysis: Calculated for $C_{17}H_{15}FN_2O_3$: %C, 65.0; %H, 4.8; %N, 8.9; Found; %C, 64.4; %H, 4.8; %N, 8.8. The structural assignment was confirmed by infrared spectral analysis.

Part J

A solution of 2.0 g of the product of Part I in 35 ml hot glacial acetic acid was treated with 40 ml of 3 N hydrochloric acid, and the mixture was heated at reflux temperature for 1 hour. The mixture was cooled and filtered, and the solid was washed with water to provide 1.7 g of 8-cyano-6,7-dihydro-9-fluoro-5-methyl-1-oxo-1H,5H-benzo[ij]quinolizine-2-carboxylic acid as a white solid, m.p. 300° C. Analysis: Calculated for $C_{15}H_{11}FN_2O_3$: %C, 62.9; %H, 3.8; %N, 9.8; Found: %C, 62.5; %H, 3.4; %N, 9.7.

EXAMPLE 10

A solution of 10.0 g (37.3 mmole) of 8-cyano-6,7-dihydro-5-methyl-1-oxo-1H,5H-benzo[ij]quinolizine-2-carboxylic acid and 37.0 ml of 1 N sodium hydroxide solution in 400 ml of water was formed by heating the mixture to 35° C. for 30 minutes. The warm solution was filtered, then lyophilized to provide 10.3 g of sodium 8-cyano-6,7-dihydro-5-methyl-1-oxo-1H,5H-benzo[ij]quinolizine-2-carboxylate hydrate as a white powder, m.p. >300° C. Analysis: Calculated for $C_{15}H_{11}NaN_2O_3.\tfrac{1}{2}H_2O$: %C, 60.2; %H, 4.0; %N, 9.3; Found: %C, 60.4; %H, 3.6; %N, 9.3.

EXAMPLE 11

A solution of 1.0 g (3.5 mmole) of 8-cyano-6,7-dihydro-9-fluoro-5-methyl-1-oxo-1H,5H-benzo[ij]quinolizine-2-carboxylic acid and 0.14 g (3.4 mmole) of sodium hydroxide in 100 ml of water was formed by heating the mixture. The solution was filtered, then lyophilized to provide 0.9 g of sodium 8-cyano-6,7-dihydro-9-fluoro-5-methyl-1-oxo-1H,5H-benzo[ij]quinolizine-2-carboxylate hydrate as a white solid, m.p. 268° C. (dec.). Analysis: Calculated for $C_{15}H_{10}FN_2NaO_3.\tfrac{1}{2}H_2O$: %C, 57.3; %H, 3.4; %N, 8.9; Found: %C, 57.2; %H, 3.2; %N, 8.9.

EXAMPLE 12

A mixture of 1.8 g of 8-cyano-6,7-dihydro-5-methyl-1-oxo-1H,5H-benzo[ij]quinolizine-2-carboxylic acid, 25 ml of thionyl chloride and 5 drops of N,N-dimethylformamide was heated on a steam bath until a solution was obtained. Evaporation to dryness gave a residue which was triturated with chloroform. The solid was isolated by filtration and suspended in 50 ml of chloroform. To this stirred solution was added, dropwise, 5 ml of N,N-dimethylaminoethanol until a solution was obtained. The solution was washed with water, dried over magnesium sulfate and evaporated to provide a tan residue. The residue was suspended in 60 ml of isopropyl alcohol and filtered. The filtrate was treated with isopropyl alcohol saturated with hydrogen chloride to provide a white solid. The product was washed with an isopropyl alcohol-diethyl ether mixture (50:50) to provide white solid N,N-dimethylaminoethyl 8-cyano-6,7-dihydro-5-methyl-1-oxo-1H,5H-benzo[ij]quinolizine-2-carboxylate hydrochloride hydrate, m.p. 260° C. (dec.). Analysis: Calculated for $C_{19}H_{21}N_3O_3.HCl.\tfrac{1}{2}H_2O$: %C, 59.3; %H, 6.0; %N, 10.9; Found: %C, 59.7; %H, 6.0; %N, 10.8. The structural assignment was confirmed by infrared spectral analysis.

EXAMPLE 13

The antibacterial activity of the 8-cyano carboxylic acids of Formula I and their sodium salts and the 10-cyano compound shown in Example 71 of U.S. Pat. No. 3,896,131 was evaluated. Activity versus both gram negative and gram positive bacteria was much higher for the compounds of the invention than for the known compound. The tests were run both in the absence and in the presence of horse serum as described hereinabove. The results (as minimum inhibitory concentration) are shown in the table below:

| Compound | Bacillus Subtilis | | Strep. Species | | Staphy. Aureus | | Esch. Coli | | Pseudomonas Aeruginosa | | Enterococcus | | Klebs. Pneumoniae | |
|---|---|---|---|---|---|---|---|---|---|---|---|---|---|---|
| 8-CN, 9-F | NA | NA | 10 | 10 | 1 | 1 | 1 | .1P | 100 | 100 | 10 | 10 | 1P | 1P |
| 8-CN, 9-F (sodium salt) | NA | NA | 1P | 1P | .1P | .1P | .1 | .1 | 100 | 100 | 1P | 10 | 1 | 1P |
| 8-CN, 9-H | 1 | 1 | 100 | 100 | 1 | 10 | 1 | 1 | 100 | 100 | 100 | 100 | 1P | .10 |
| 10-CN (prior art) | 100 | 100 | I | I | 100 | 100 | 1 | 1 | I | I | I | I | 1P | 10P |

NA = Not available
I = Inactive
P = Partial

In 8 of 14 measurements the 8-cyano compounds of the invention are from ten to one hundred times more potent than the 10-cyano compound of the prior art. In one additional measurement, the 8-cyano compounds are from 2 to 9 times as potent as the 10-cyano compound. In the remaining 5 of 14 measurements the 8-cyano compounds are at least equal to the 10-cyano compound, and some are better.

EXAMPLE 14

In in vivo tests of the 10-cyano compound of the prior art compared to the 8-cyano, 9-hydrogen compound of the invention and its salt, the 10-cyano compound was found to be ineffective in protecting the animals against lethal infection, while the 8-cyano compound and its salt were found to be effective in protecting the animals at comparable (and safe) dose levels. The actual data are set forth in the following table.

| Compound | Dose (Mg/Kg) | Survivors, Days Post Infection | | | | | Infecting Organism |
|---|---|---|---|---|---|---|---|
| | | 0 | 1 | 2 | 3 | 5 | |
| 8-CN, 9-H | 25/10 | 10/10 | 10/10 | 10/10 | NA | 10/9 | Klebsiella Pneumoniae |
| " | 50/25 | 10/10 | 7/3 | 7/3 | 7/3 | 7/3 | Staphylococcus Aureus |
| 8-CN, 9-H (Na Salt) | 25/10 | 10/10 | 10/10 | 10/10 | NA | 10/10 | Klebsiella Pneumoniae |
| 8-CN, 9-H (Na Salt) | 50/25 | 10/10 | 10/7 | 10/7 | 10/7 | 10/7 | Staphylococcus Aureus |
| 10-CN (Prior Art) | 25/10 | 10/10 | 2/1 | 0/1 | NA | 0/1 | Klebsiella Pneumoniae |
| 10-CN (Prior art) | 50/25 | 10/10 | 0/0 | 0/0 | 0/0 | 0/0 | Staphylococcus Aureus |

What is claimed is:

1. A compound of the formula:

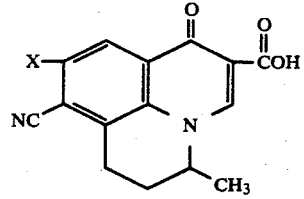

wherein X is hydrogen or fluorine, or a pharmaceutically acceptable carboxylate salt thereof, an alkyl or alkylaminoalkyl ester thereof where the alkyl group contains 1 to 4 carbon atoms, an alkylaminoalkyl ester salt thereof where the alkyl group contains 1 to 4 carbon atoms, an acyl chloride thereof, or an amide thereof having the formula —NR$_1$R$_2$ where R$_1$ and R$_2$ are independently hydrogen or an alkyl group containing 1 to 4 carbon atoms.

2. The compound 8-cyano-6,7-dihydro-5-methyl-1-oxo-1H,5H-benzo[ij]quinolizine-2-carboxylic acid or a pharmaceutically acceptable carboxylate salt thereof according to claim 1.

3. The compound 8-cyano-6,7-dihydro-9-fluoro-5-methyl-1-oxo-1H,5H-benzo[ij]quinolizine-2-carboxylic acid or a pharmaceutically acceptable carboxylate salt thereof according to claim 1.

4. A method of inhibiting the growth of microorganisms by contacting said microorganisms with an effective amount of a compound according to claim 1.

5. A composition for inhibiting the growth of microorganisms comprising an effective amount of the compound according to claim 1 formulated in a pharmaceutically-acceptable vehicle.

* * * * *